United States Patent [19]

Wong

[11] 4,393,068
[45] Jul. 12, 1983

[54] PYRIDYLALKYL THIOCARBONATES AS INSECT REPELLENTS

[76] Inventor: Rayman Y. Wong, 3411 Lowell Ave., Richmond, Calif. 94804

[21] Appl. No.: 337,039

[22] Filed: Jan. 4, 1982

[51] Int. Cl.³ .................. A01N 43/40; C07D 213/46
[52] U.S. Cl. ..................................... 424/263; 546/340
[58] Field of Search ...................... 546/340; 424/263

[56] References Cited

U.S. PATENT DOCUMENTS 4,038,435 7/1977 Winter et al. .................. 546/340

FOREIGN PATENT DOCUMENTS 485786 7/1980 Spain .................................. 546/340

Primary Examiner—Henry R. Jiles
Assistant Examiner—Robert C. Whittenbaugh
Attorney, Agent, or Firm—Joel G. Ackerman

[57] ABSTRACT

Novel compounds having the formula

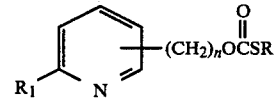

in which R is alkyl, cycloalkyl, aralkyl, chlorophenyl or chlorobenzyl, $R_1$ is hydrogen or lower alkyl and n is 1, 2, or 3, are insect repellents.

84 Claims, No Drawings

PYRIDYLALKYL THIOCARBONATES AS INSECT REPELLENTS

This invention relates to novel compounds having the formula

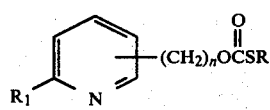

in which R is alkyl, cycloalkyl, aralkyl, chlorophenyl or chlorobenzyl, $R_1$ is hydrogen or lower alkyl and n is 1, 2, or 3. If R is hydrogen, the side chain may be substituted on the pyridine ring at the 2-, 3-, or 4-position; if R is lower alkyl the side chain may be substituted at the 2-position.

The term "alkyl" refers to straight- or branched-chain saturated hydrocarbyl moieties having from 1–20, preferably 1–12, carbon atoms. "Lower alkyl" refers to such moieties having from 1–4 carbon atoms. The term "cycloalkyl" refers to cyclic saturated hydrocarbyl moieties having from 3–7 carbon atoms, for instance, cyclohexyl. The term "aralkyl" refers to aromatic moieties, bonded to an aliphatic (straight- or branched-chain) moiety, preferably having from 1–3, most preferably 1 or 2, carbon atoms, for instance, benzyl and phenethyl.

The compounds have utility as insect repellents, particularly for repelling flying insects from lighting and/or feeding.

The compounds of this type can be prepared by reaction of an appropriate pyridyl alkanol with an appropriate chlorothioformate;

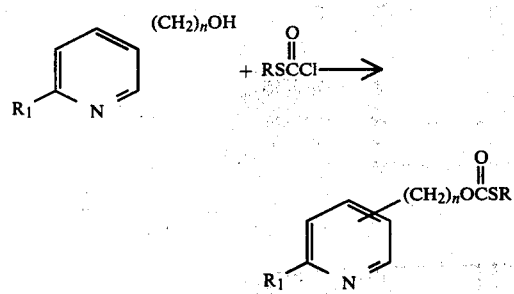

The pyridyl alkanols in which R is lower alkyl, if not commercially available, can be synthesized, for example, by the method of Umezawa et al., Japanese patent application No. 74/13180.

The reaction is generally conducted at temperatures of about 0° C. to about 25° C. in the presence of a solvent such as methylene chloride and a hydrogen chloride acceptor such as sodium bicarbonate, triethylamine, or pyridine. The product is recovered by conventional extraction, washing, filtration, and other purification steps as may be necessary. Optionally, the hydrogen chloride acceptor may be added after the reaction has gone to completion.

Preparation of such compounds is illustrated by the following example.

Preparation of S-methyl, O-[3-(3-pyridyl)-1-propyl] Thiocarbonate (Compound 1 herein)

In a flask were placed 5.0 grams (g.) (0.0364 mole) 3-(3-pyridyl)-1-propanol and 50 milliliters (ml.) methylene chloride. The flask was cooled to 0° C. There was then added, with stirring, 4.4 g. (0.04 mole) methyl chlorothioformate, at such a rate as to maintain the temperature at a maximum of 15° C. After addition was complete, the mixture was stirred for 1 hour at room temperature.

The product was neutralized with saturated sodium bicarbonate, then washed with water and saturated sodium chloride, and dried over sodium sulfate. The dried solution was filtered and the solvent removed in vacuo, producing 6.2 g. (82% of theoretical yield) of the desired product, a clear, yellow oil, $n_D^{30}$ 1.5335. The structure of the product was confirmed by infrared (ir), nuclear magnetic resonance (nmr) and mass spectroscopy (ms).

The following Table I contains a list of representative compounds of this invention.

TABLE I

| Compound No. | $R_1$ | R | ring position | n | $n_D^{30}$ |
|---|---|---|---|---|---|
| 1 | H | methyl | 3- | 3 | 1.5335 |
| 2 | H | ethyl | 3- | 3 | 1.5420 |
| 3 | H | isopropyl | 3- | 3 | 1.5110 |
| 4 | H | n-propyl | 3- | 3 | 1.5165 |
| 5 | H | n-butyl | 3- | 3 | 1.5115 |
| 6 | H | sec.-butyl | 3- | 3 | 1.5145 |
| 7 | H | isobutyl | 3- | 3 | 1.5146 |
| 8 | H | tert.-butyl | 3- | 3 | 1.5122 |
| 9 | H | 3-methylbutyl | 3- | 3 | 1.5120 |
| 10 | H | n-hexyl | 3- | 3 | 1.5077 |
| 11 | H | cyclohexyl | 3- | 3 | 1.5720 |
| 12 | H | $C(CH_3)_2C_2H_5$ | 3- | 3 | 1.5127 |
| 13 | H | p-chlorophenyl | 3- | 3 | 1.5838 |
| 14 | H | n-dodecyl | 3- | 3 | 1.4964 |
| 15 | H | benzyl | 3- | 3 | 1.5615 |
| 16 | H | 2-methylbutyl | 3- | 3 | 1.5030 |
| 17 | H | ethyl | 4- | 3 | 1.5380 |
| 18 | methyl | ethyl | 2- | 3 | 1.5145 |
| 19 | H | methyl | 2- | 3 | 1.5610 |
| 20 | methyl | methyl | 2- | 3 | 1.5191 |
| 21 | H | n-propyl | 4- | 3 | 1.5126 |
| 22 | methyl | n-propyl | 2- | 3 | 1.5100 |
| 23 | H | isopropyl | 4- | 3 | 1.5431 |
| 24 | methyl | isopropyl | 2- | 3 | 1.5047 |
| 25 | H | n-butyl | 4- | 3 | 1.5286 |
| 26 | methyl | n-butyl | 2- | 3 | 1.5029 |
| 27 | methyl | sec.-butyl | 2- | 3 | 1.5041 |
| 28 | H | sec.-butyl | 4- | 3 | 1.5016 |
| 29 | methyl | isobutyl | 2- | 3 | 1.5021 |
| 31 | methyl | tert.-butyl | 2- | 3 | 1.5027 |
| 32 | H | tert.-butyl | 4- | 3 | 1.5177 |
| 33 | H | methyl | 2- | 3 | 1.5230 |
| 34 | H | ethyl | 2- | 3 | 1.5167 |
| 35 | H | isopropyl | 2- | 3 | 1.5102 |
| 36 | H | n-butyl | 2- | 3 | 1.5070 |
| 37 | H | sec.-butyl | 2- | 3 | 1.5073 |
| 38 | H | isobutyl | 2- | 3 | 1.5087 |
| 39 | H | n-propyl | 2- | 3 | 1.5141 |
| 40 | H | tert.-butyl | 2- | 3 | 1.5067 |
| 41 | H | benzyl | 4- | 3 | 1.5750 |
| 42 | H | benzyl | 2- | 3 | 1.5664 |
| 43 | methyl | benzyl | 2- | 3 | 1.5602 |
| 44 | H | phenethyl | 2- | 3 | 1.5581 |
| 45 | H | phenethyl | 4- | 3 | 1.5572 |

TABLE I-continued

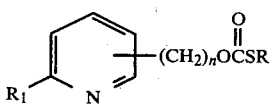

| Compound No. | R₁ | R | ring position | n | $n_D^{30}$ |
|---|---|---|---|---|---|
| 46 | H | phenethyl | 3- | 3 | 1.5560 |
| 47 | methyl | phenethyl | 2- | 3 | 1.5535 |
| 48 | H | p-chlorophenyl | 4- | 3 | 1.5766 |
| 49 | H | p-chlorophenyl | 2- | 3 | 1.5756 |
| 50 | methyl | p-chlorophenyl | 2- | 3 | 1.5742 |
| 51 | H | n-octyl | 4- | 3 | 1.5018 |
| 52 | H | n-octyl | 3- | 3 | 1.5023 |
| 53 | H | n-octyl | 2- | 3 | 1.5015 |
| 54 | methyl | n-octyl | 2- | 3 | 1.5000 |
| 55 | H | tert.-butyl | 3- | 1 | 1.5228 |
| 56 | H | tert.-butyl | 2- | 2 | 1.5011 |
| 57 | H | isopropyl | 3- | 1 | 1.5191 |
| 58 | H | isopropyl | 2- | 2 | 1.5125 |
| 59 | H | p-chlorobenzyl | 3- | 3 | 1.5603 |

The structures of the compounds in the foregoing Table I were confirmed by ir, nmr, and/or ms.

INSECT REPELLENT TESTS

Compounds described in the above Table I were tested for insect repellency by the following procedures:

Mosquitoes

A paper cup filled with pupae of the mosquito *Culex pipiens quinquefasciatus* (Say) was placed in a screened cage and the pupae allowed to emerge into adults. Sugar cubes were then saturated with 1.0 milliliter (ml.) of an acetone solution containing 0.1 wt.% of the test compound, and, for a control, with the same amount of acetone alone. After the cubes dried they were put into the screened cage. Repellency was determined by the number of mosquito adults lighting and feeding on the sugar cubes, with observations being made daily for 5 days after treatment. The number of days of complete repellency of mosquitoes from the sugar cubes was recorded.

Comparative tests were similarly conducted using the compound N,N-diethyl-m-toluamide, commercially manufactured and employed as an insect repellent, generally known by the generic name "deet." The results of the tests of deet and the compounds of Table I are shown in the following Table II. The numbers in each column represent the number of days of complete repellency observed using the specified concentration.

TABLE II

| (Southern House Mosquito) | |
|---|---|
| Compound | Days Repelled, 0.1 wt. % |
| 1 | 11 |
| 2 | 11 |
| 3 | >5 |
| 4 | >5 |
| 5 | >5 |
| 6 | >5 |
| 7 | >5 |
| 8 | >5 |
| 9 | 3.5 |
| 10 | 3 |
| 11 | 3 |
| 12 | 4.5 |
| 13 | 3 |
| 14 | 2 |
| 17 | 1 |

TABLE II-continued

| (Southern House Mosquito) | |
|---|---|
| Compound | Days Repelled, 0.1 wt. % |
| 18 | >3 |
| 19 | 1 |
| deet | 1 |
| control | 0 |

Houseflies

The insect utilized for this test was the housefly, *Musca domestica* (L.). One hundred houseflies of mixed sexes were placed in test cages. In each cage was placed a sugar cube saturated with 1.0 ml of acetone containing 1 wt.% of the test compound. The cube was dried and weighed before being placed in the cage. Each cage also contained a water-saturated cotton plug, to provide moisture. The test cages were placed on a turntable and rotated at 1.5 revolutions per minute to keep the flies randomly distributed inside the cage. After 48 hours the flies in each cage were anesthetized with carbon dioxide. The sugar cubes were removed and reweighed and the percentage weight loss (due to consumption by the flies) recorded. A repellency ratio, calculated as the percent weight loss of the treated sugar cube divided by the percent weight loss of a control sugar cube treated with acetone only was calculated. The lower the repellency ratio, the greater the repellency of the test compound. The repellency ratios of the test compounds are shown in the following Table III. Values given for the repellency ratio represent an average of from one to three replications per compound.

TABLE III

| (Housefly) | |
|---|---|
| Compound | Repellency Ratio; Concentration, 1 wt. % |
| 1 | 0.48 |
| 2 | 0.37 |
| 3 | 0.38 |
| 4 | 0.38 |
| 5 | 0.39 |
| 6 | 0.33 |
| 7 | 0.38 |
| 8 | 0.37 |
| 9 | 0.25 |
| 10 | 0.29 |
| 11 | 0.40 |
| 12 | 0.18 |
| 13 | 0.57 |
| 14 | 0.66 |
| 17 | 0.18 |
| 18 | 0.36 |
| 19 | 0.42 |
| 20 | 0.46 |
| 21 | 0.24 |
| 22 | 0.36 |
| 23 | 0.54 |
| 24 | 0.34 |
| 25 | 0.38 |
| 26 | 0.36 |
| 27 | 0.31 |
| 28 | 0.19 |
| 29 | 0.52 |
| 30 | 0.37 |
| 31 | 0.35 |
| 32 | 0.27 |
| 33 | 0.61 |
| 34 | 0.37 |
| 35 | 0.28 |
| 36 | 0.37 |
| 37 | 0.18 |
| 38 | 0.32 |
| 39 | 0.43 |
| 40 | 0.31 |
| 41 | 0.43 |

TABLE III-continued

| Compound | (Housefly) Repellency Ratio; Concentration, 1 wt. % |
|---|---|
| 42 | 0.51 |
| 43 | 0.64 |
| 44 | 0.52 |
| 45 | 0.68 |
| 46 | 0.37 |
| 47 | 0.64 |
| 49 | 0.50 |
| 50 | 0.55 |
| 51 | 0.32 |
| 52 | 0.37 |
| 53 | 0.54 |
| 54 | 0.58 |
| 55 | 0.26 |
| 56 | 0.37 |
| 57 | 0.32 |
| 58 | 0.37 |
| 59 | 0.35 |
| deet | 0.60 |

Thus at a concentration of 1% by weight, the test compounds repelled insects to the extent that the weight loss of sugar cubes treated with those compounds was generally less than 50% of that of the control (untreated) cubes.

Stable Fly; Yellow Fever Mosquito

Insects utilized for these tests were the stable fly, *Stomoxys calcitrans* and yellow fever mosquito, *Aedes aegypti.*

Pupae of these insects were placed in separate standard fly cages and allowed to emerge into adult. The mosquitoes were supplied with a sugar-water solution; the stable flies with water, sugar cubes, and casein. Tests on mosquitoes were performed at least three days after the adults emerged; those on stable flies, one day after emergence because of the short life span (4–5 days) of these flies without a blood meal.

Test compounds were weighed and dissolved in acetone. One milliliter (ml) of the test solution was precipitated onto a 9×9 cm. swatch of cotton stocking. The swatches were then allowed to dry for 1 hour.

A square opening 6×6 cm. was made in an upper corner of one side of each fly cage. A large, hard cardboard disk was placed over the opening so that it could be rotated to either cover or expose the opening as desired. One-half of the disc was left intact. In the remaining half, several 6×6 cm. square openings were cut. When the intact half of this disc was located over the opening in the fly cage, this opening was effectively sealed.

Swatches of treated stocking were placed over the square holes in the disc and held in place by metal frames attached to magnetic tape.

To initiate the test, the disc was rotated so that a treated swatch became located over the opening in the cage. The palm of the tester's hand was placed over a cardboard ring, 8 cm. in diameter and 1 cm. thick. The ring acted as a spacer and protected the hand from bites which could otherwise be inflicted by the insects. A breath of air was exhaled through tubing into the opening, so that insects could be attracted to the swatch by the warm, moist air and the tester's hand. The number of insects landing on the swatch was observed, and the number probing, recorded during a 1-minute exposure. Repellency was considered to occur when 5 or fewer insects probed the swatch during the exposure.

The compounds were tested at applications rates ranging from 0.1 mg/cm² of swatch downwards. The results of these tests on stable flies (SF) and yellow fever mosquitoes (YFM) are contained in Table IV.

TABLE IV

| (Stable Fly, Yellow Fever Mosquito) | | |
|---|---|---|
| | Repellent Concentration, mg/cm² | |
| Compound | SF | YFM |
| 1 | 0.03 | 0.1 |
| 2 | 0.03 | 0.1 |
| 15 | >0.1 | >0.1 |
| 16 | >0.1 | >0.1 |
| 20 | >0.1 | >0.1 |
| 21 | 0.1 | >0.1 |
| 22 | >0.1 | >0.1 |
| 23 | >0.1 | >0.1 |
| 24 | >0.1 | >0.1 |
| 25 | >0.1 | >0.1 |
| 26 | >0.1 | >0.1 |
| 27 | >0.1 | >0.1 |
| 28 | >0.1 | >0.1 |
| 29 | >0.1 | >0.1 |
| 30 | >0.1 | >0.1 |
| 31 | >0.1 | 0.1 |
| 32 | >0.1 | >0.1 |
| 33 | >0.1 | >0.1 |
| 34 | >0.1 | 0.03 |
| 35 | >0.1 | 0.03 |
| 36 | >0.1 | >0.1 |
| 37 | >0.1 | 0.03 |
| 38 | >0.1 | 0.03 |
| 39 | >0.1 | 0.03 |
| 40 | >0.1 | 0.1 |
| 41 | >0.1 | >0.1 |
| 42 | >0.1 | >0.1 |
| 43 | >0.1 | >0.1 |
| 44 | >0.1 | >0.1 |
| 45 | >0.1 | >0.1 |
| 46 | >0.1 | >0.1 |
| 47 | >0.1 | >0.1 |
| 48 | >0.1 | >0.1 |
| 49 | >0.1 | >0.1 |
| 50 | >0.1 | >0.1 |
| 51 | >0.1 | >0.1 |
| 52 | >0.1 | >0.1 |
| 53 | >0.1 | >0.1 |
| 54 | >0.1 | >0.1 |
| 59 | >0.1 | — |

Black Blowfly, Hornfly

Compounds 1 and 2 were tested for repellent activity against the black blowfly, *Phormia regina* and the hornfly, *Haematobia irritans.* The blowfly tests were conducted similarly to those on the housefly; the hornfly tests were conducted similarly to those on the stable fly. Results are reported in Table V below.

TABLE V

| Compound No. | Black blowfly, repellency ratio, 0.1 wt. % | Hornfly repellent concentration, mg/cm² |
|---|---|---|
| 1 | 0.42 | 0.1 |
| 2 | 0.54 | 0.03 |

The novel compounds of this invention may be used as insect repellents in either diluted or undiluted form. When used in a diluted form, the compounds may be embodied in compositions containing relatively high or relatively low concentrations of the active compound. For example, the active compound can be incorporated into relatively high concentration compositions such as wet sprays or solutions in alcohol or other suitable solvents. Such compositions may contain, in addition to the active compound, adjuvants such as emulsifying agents, surface active agents, anti-oxidants and propellants which may be found normally in insect repellent preparations. The active compounds of this invention may be employed as the sole active component of such compositions or may be used in admixture with other compounds having a similar or different utility. For example, the compounds may be incorporated into creams, lotions, powders, suntan oil, insecticides and other preparations which may contain pesiticidal or other useful substances, as well as into compositions of various types used for treating fabrics or articles of clothing to render them insect repellent. In general, compositions for repellent use may contain from 0.5 to up to 80 weight %, preferably from 2 to about 40 weight %, of the novel active compounds. High concentration formulations, containing up to 95% of the compounds, could also be utilized for low-volume spraying from the air.

Examples of typical formulations employing compounds of this invention are for instance,

EXAMPLE 1

Emulsifiable Concentrate

| Component | Weight % |
| --- | --- |
| Compound 1 | 53.6 |
| Aromatic Hydrocarbon Solvent | 36.4 |
| Emulsifier | 10.0 |
| Total | 100.0 |

EXAMPLE 2

Lotion

| Component | Weight % |
| --- | --- |
| Compound 37 | 10.7 |
| Lanolin | 4.8 |
| Mineral oil | 8.0 |
| Trihydroxyethylamine stearate | 1.8 |
| Glycosterin | 0.8 |
| Glycerine | 4.6 |
| Sodium benzoate | 1.0 |
| Water | 68.3 |
| Total | 100.0 |

EXAMPLE 3

Alcohol Solution

| Component | Weight % |
| --- | --- |
| Compound 38 | 53.6 |
| Isopropanol | 46.4 |
| Total | 100.0 |

EXAMPLE 4

Alcohol Solution

| Component | Weight % |
| --- | --- |
| Compound 39 | 80.0 |
| Ethanol | 20.0 |
| Total | 100.0 |

EXAMPLE 5

Wettable Powder

| Component | Weight % |
| --- | --- |
| Compound 2 | 26.9 |
| Hydrated calcium silicate | 62.1 |
| Sodium lignosulfonate | 5.0 |
| Orzan A (mixture of ammonium lignosulfonate and wood sugars) | 5.0 |
| Wetting agent | 1.0 |

EXAMPLE 5-continued

Wettable Powder

| Component | Weight % |
| --- | --- |
| Total | 100.0 |

What is claimed is:

1. A compound having the formula

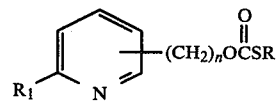

in which R is alkyl, cycloalkyl, aralkyl, wherein alkyl is a group containing up to 20 carbon atoms chlorophenyl or chlorobenzyl, $R_1$ is hydrogen or lower alkyl, and n is 1, 2, or 3.

2. A compound according to claim 1 in which $R_1$ is hydrogen.

3. A compound according to claim 1 in which $R_1$ is methyl.

4. A compound according to claim 1 in which R is alkyl wherein alkyl is a group containing up to 20 carbon atoms.

5. A compound according to claim 1 in which the side chain is substituted on the pyridine ring at the 2-position.

6. A compound according to claim 1 in which the side chain is substituted on the pyridine ring at the 3-position.

7. A compound according to claim 1 in which the side chain is substituted on the pyridine ring at the 4-position.

8. A compound according to claim 1 in which $R_1$ is hydrogen, R is methyl, n is 3 and the side chain is substituted on the pyridine ring at the 3-position.

9. A compound according to claim 1 in which $R_1$ is hydrogen, R is ethyl, n is 3 and the side chain is substituted on the pyridine ring at the 3-position.

10. A compound according to claim 1 in which $R_1$ is hydrogen, R is isopropyl, n is 3 and the side chain is substituted on the pyridine ring at the 3-position.

11. A compound according to claim 1 in which $R_1$ is hydrogen, R is n-propyl, n is 3 and the side chain is substituted on the pyridine ring at the 3-position.

12. A compound according to claim 1 in which $R_1$ is hydrogen, R is n-butyl, n is 3 and the side chain is substituted on the pyridine ring at the 3-position.

13. A compound according to claim 1 in which $R_1$ is hydrogen, R is sec.-butyl, n is 3 and the side chain is substituted on the pyridine ring at the 3-position.

14. A compound according to claim 1 in which $R_1$ is hydrogen, R is isobutyl, n is 3 and the side chain is substituted on the pyridine ring at the 3-position.

15. A compound according to claim 1 in which $R_1$ is hydrogen R is tert.-butyl, n is 3 and the side chain is substituted on the pyridine ring at the 3-position.

16. A compound according to claim 1 in which $R_1$ is hydrogen, R is 3-methylbutyl, n is 3 and the side chain is substituted on the pyridine ring at the 3-position.

17. A compound according to claim 1 in which $R_1$ is hydrogen, R is n-hexyl, n is 3 and the side chain is substituted on the pyridine ring at the 3-position.

18. A compound according to claim 1 in which $R_1$ is hydrogen, R is cyclohexyl, n is 3 and the side chain is substituted on the pyridine ring at the 3-position.

19. A compound according to claim 1 in which $R_1$ is hydrogen, R is $C(CH_3)_2C_2H_5$, n is 3 and the side chain is substituted on the pyridine ring at the 3-position.

20. A compound according to claim 1 in which $R_1$ is hydrogen, R is p-chlorophenyl, n is 3 and the side chain is substituted on the pyridine ring at the 3-position.

21. A compound according to claim 1 in which $R_1$ is hydrogen, R is n-dodecyl, n is 3 and the side chain is substituted on the pyridine ring at the 3-position.

22. A compound according to claim 1 in which $R_1$ is hydrogen, R is benzyl, n is 3 and the side chain is substituted on the pyridine ring at the 3-position.

23. A compound according to claim 1 in which $R_1$ is hydrogen, R is 2-methylbutyl, n is 3 and the side chain is substituted on the pyridine ring at the 3-position.

24. A compound according to claim 1 in which $R_1$ is hydrogen R is ethyl, n is 3 and the side chain is substituted on the pyridine ring at the 4-position.

25. A compound according to claim 1 in which $R_1$ is methyl, R is ethyl, n is 3 and the side chain is substituted on the pyridine ring at the 2-position.

26. A compound according to claim 1 in which $R_1$ is hydrogen, R is methyl, n is 3 and the side chain is substituted on the pyridine ring at the 2-position.

27. A compound according to claim 1 in which $R_1$ is methyl, R is methyl, n is 3 and the side chain is substituted on the pyridine ring at the 2-position.

28. A compound according to claim 1 in which $R_1$ is hydrogen, R is n-propyl, n is 3 and the side chain is substituted on the pyridine ring at the 4-position.

29. A compound according to claim 1 in which $R_1$ is methyl, R is n-propyl, n is 3 and the side chain is substituted on the pyridine ring at the 2-position.

30. A compound according to claim 1 in which $R_1$ is hydrogen, R is isopropyl, n is 3 and the side chain is substituted on the pyridine ring at the 4-position.

31. A compound according to claim 1 in which $R_1$ is methyl, R is isopropyl, n is 3 and the side chain is substituted on the pyridine ring at the 2-position.

32. A compound according to claim 1 in which $R_1$ is hydrogen, R is n-butyl, n is 3 and the side chain is substituted on the pyridine ring at the 4-position.

33. A compound according to claim 1 in which $R_1$ is methyl, R is n-butyl, n is 3 and the side chain is substituted on the pyridine ring at the 2-position.

34. A compound according to claim 1 in which $R_1$ is methyl, R is sec.-butyl, n is 3 and the side chain is substituted on the pyridine ring at the 2-position.

35. A compound according to claim 1 in which $R_1$ is hydrogen, R is sec.-butyl, n is 3 and the side chain is substituted on the pyridine ring at the 4-position.

36. A compound according to claim 1 in which $R_1$ is methyl, R is isobutyl, n is 3 and the side chain is substituted on the pyridine ring at the 2-position.

37. A compound according to claim 1 in which $R_1$ is hydrogen, R is isobutyl, n is 3 and the side chain is substituted on the pyridine ring at the 4-position.

38. A compound according to claim 1 in which $R_1$ is methyl, R is tert.-butyl, n is 3 and the side chain is substituted on the pyridine ring at the 2-position.

39. A compound according to claim 1 in which $R_1$ is hydrogen, R is tert.-butyl, n is 3 and the side chain is substituted on the pyridine ring at the 4-position.

40. A compound according to claim 1 in which $R_1$ is hydrogen, R is methyl, n is 3 and the side chain is substituted on the pyridine ring at the 2-position.

41. A compound according to claim 1 in which $R_1$ is hydrogen, R is ethyl, n is 3 and the side chain is substituted on the pyridine ring at the 2-position.

42. A compound according to claim 1 in which $R_1$ is hydrogen, R is isopropyl, n is 3 and the side chain is substituted on the pyridine ring at the 2-position.

43. A compound according to claim 1 in which $R_1$ is hydrogen, R is n-butyl, n is 3 and the side chain is substituted on the pyridine ring at the 2-position.

44. A compound according to claim 1 in which $R_1$ is hydrogen, R is sec.-butyl, n is 3 and the side chain is substituted on the pyridine ring at the 2-position.

45. A compound according to claim 1 in which $R_1$ is hydrogen, R is isobutyl, n is 3 and the side chain is substituted on the pyridine ring at the 2-position.

46. A compound according to claim 1 in which $R_1$ is hydrogen, R is n-propyl, n is 3 and the side chain is substituted on the pyridine ring at the 2-position.

47. A compound according to claim 1 in which $R_1$ is hydrogen, R is tert.-butyl, n is 3 and the side chain is substituted on the pyridine ring at the 2-position.

48. A compound according to claim 1 in which $R_1$ is hydrogen, R is benzyl, n is 3 and the side chain is substituted on the pyridine ring at the 4-position.

49. A compound according to claim 1 in which $R_1$ is hydrogen, R is benzyl, n is 3 and the side chain is substituted on the pyridine ring at the 2-position.

50. A compound according to claim 1 in which $R_1$ is methyl, R is benzyl, n is 3 and the side chain is substituted on the pyridine ring at the 2-position.

51. A compound according to claim 1 in which $R_1$ is hydrogen, R is phenethyl, n is 3 and the side chain is substituted on the pyridine ring at the 2-position.

52. A compound according to claim 1 in which $R_1$ is hydrogen, R is phenethyl, n is 3 and the side chain is substituted on the pyridine ring at the 4-position.

53. A compound according to claim 1 in which $R_1$ is hydrogen, R is phenethyl, n is 3 and the side chain is substituted on the pyridine ring at the 3-position.

54. A compound according to claim 1 in which $R_1$ is methyl, R is phenethyl, n is 3 and the side chain is substituted on the pyridine ring at the 2-position.

55. A compound according to claim 1 in which $R_1$ is methyl, R is p-chlorophenyl, n is 3 and the side chain is substituted on the pyridine ring at the 4-position.

56. A compound according to claim 1 in which $R_1$ is hydrogen, R is p-chlorophenyl, n is 3 and the side chain is substituted on the pyridine ring at the 2-position.

57. A compound according to claim 1 in which $R_1$ is methyl, R is p-chlorophenyl, n is 3 and the side chain is substituted on the pyridine ring at the 2-position.

58. A compound according to claim 1 in which $R_1$ is hydrogen, R is n-octyl, n is 3 and the side chain is substituted on the pyridine ring at the 4-position.

59. A compound according to claim 1 in which $R_1$ is hydrogen, R is n-octyl, n is 3 and the side chain is substituted on the pyridine ring at the 3-position.

60. A compound according to claim 1 in which $R_1$ is hydrogen, R is n-octyl, n is 3 and the side chain is substituted on the pyridine ring at the 2-position.

61. A compound according to claim 1 in which $R_1$ is methyl, R is n-octyl, n is 3 and the side chain is substituted on the pyridine ring at the 2-position.

62. A compound according to claim 1 in which $R_1$ is hydrogen, R is tert.-butyl, n is 1 and the side chain is substituted on the pyridine ring at the 3-position.

63. A compound according to claim 1 in which $R_1$ is hydrogen, R is tert.-butyl, n is 2 and the side chain is substituted on the pyridine ring at the 2-position.

64. A compound according to claim 1 in which $R_1$ is hydrogen, R is isopropyl, n is 1 and the side chain is substituted on the pyridine ring at the 3-position.

65. A compound according to claim 1 in which $R_1$ is hydrogen, R is isopropyl, n is 2 and the side chain is substituted on the pyridine ring at the 2-position.

66. A compound according to claim 1 in which $R_1$ is hydrogen, R is p-chlorobenzyl, n is 3 and the side chain is substituted on the pyridine ring at the 3-position.

67. A method of repelling insects from a locus to be protected therefrom, comprising applying to said locus an effective insect repelling amount of a compound having the formula

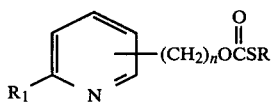

in which R is alkyl, cycloalkyl, aralkyl, wherein alkyl is a group containing up to 20 carbon atoms chlorophenyl or chlorobenzyl, $R_1$ is hydrogen or lower alkyl, and n is 1, 2, or 3.

68. A method according to claim 67 in which $R_1$ is hydrogen.

69. A method according to claim 67 in which $R_1$ is methyl.

70. A method according to claim 67 in which R is alkyl wherein alkyl is a group containing up to 20 carbon atoms.

71. A method according to claim 67 in which the side chain is substituted on the pyridine ring at the 2-position.

72. A method according to claim 67 in which the side chain is substituted on the pyridine ring at the 3-position.

73. A method according to claim 67 in which the side chain is substituted on the pyridine ring at the 4-position.

74. A method according to claim 67 in which the insect is the housefly.

75. A method according to claim 67 in which the insect is yellow fever mosquito.

76. A method according to claim 67 in which the insect is stable fly.

77. A method according to claim 67 in which R is methyl, $R_1$ is hydrogen, n is 3 and the side chain is substituted on the pyridine ring at the 3-position.

78. A method according to claim 67 in which R is ethyl, $R_1$ is hydrogen, n is 3 and the side chain is substituted on the pyridine ring at the 3-position.

79. A method according to claim 67 in which R is ethyl, $R_1$ is hydrogen, n is 3 and the side chain is substituted on the pyridine ring at the 2-position.

80. A method according to claim 67 in which R is isopropyl, $R_1$ is hydrogen, n is 3 and the side chain is substituted on the pyridine ring at the 2-position.

81. A method according to claim 67 in which R is sec.-butyl, $R_1$ is hydrogen, n is 3 and the side chain is substituted on the pyridine ring at the 2-position.

82. A method according to claim 67 in which R is isobutyl, $R_1$ is hydrogen, n is 3 and the side chain is substituted on the pyridine ring at the 2-position.

83. A method according to claim 67 in which R is n-propyl, $R_1$ is hydrogen, n is 3 and the side chain is substituted on the pyridine ring at the 2-position.

84. An insect repellent composition comprising:
(a) an amount of a compound having the formula

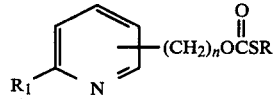

in which R is alkyl, cycloalkyl, aralkyl wherein alkyl is a group containing up to 20 carbon atoms, chlorophenyl or chlorobenzyl, $R_1$ is hydrogen or lower alkyl, and n is 1, 2, or 3, effective to repel insects; and
(b) an inert diluent or carrier suitable for insect repellent use.

* * * * *

UNITED STATES PATENT AND TRADEMARK OFFICE
CERTIFICATE OF CORRECTION

PATENT NO. : 4,393,068
DATED : July 12, 1983
INVENTOR(S) : Rayman Y. Wong

It is certified that error appears in the above-identified patent and that said Letters Patent is hereby corrected as shown below:

On the title page the following should be added:

-- [73] Assignee: Stauffer Chemical Company,
Westport, Conn. --

Signed and Sealed this

Thirtieth Day of April 1985

[SEAL]

Attest:

DONALD J. QUIGG

Attesting Officer

Acting Commissioner of Patents and Trademarks